United States Patent [19]

Lerch

[11] Patent Number: 5,800,436
[45] Date of Patent: Sep. 1, 1998

[54] DEVICE FOR POSTOPERATIVE FIXATION BACK INTO THE CRANIUM OF A PLUG OF BONE REMOVED THEREFROM DURING A SURGICAL OPERATION

[76] Inventor: Karl-Dieter Lerch, Nordstrasse 16, D-58452, Witten, Bundesrepublik, Germany

[21] Appl. No.: 790,071

[22] Filed: Jan. 28, 1997

[30] Foreign Application Priority Data

Feb. 3, 1996 [DE] Germany .................. 196 03 887.1

[51] Int. Cl.⁶ ............................................. A61B 17/68
[52] U.S. Cl. ............................................. 606/72
[58] Field of Search ......................... 606/72, 71, 70, 606/69, 73, 76, 213, 215, 216, 232

[56] References Cited

U.S. PATENT DOCUMENTS

| 3,741,205 | 6/1973 | Markolf et al. ............... 606/69 |
|---|---|---|
| 5,167,665 | 12/1992 | McKinney ............... 606/75 |
| 5,342,393 | 8/1994 | Stack ............... 606/213 |
| 5,350,399 | 9/1994 | Erlebacher et al. ............... 606/213 |
| 5,549,620 | 8/1996 | Bremer ............... 606/151 |

FOREIGN PATENT DOCUMENTS 1600713  10/1990  U.S.S.R. ............... 606/213

Primary Examiner—Guy V. Tucker
Attorney, Agent, or Firm—Max Fogiel

[57] ABSTRACT

A device for postoperative fixation back into the cranium of a plug of bone removed therefrom during a surgical operation. The device comprises a pin (11) and two concavoconvex disks (21 & 22) of a physiologically compatible metal or metal compound. The pin has a flat head (111) at one end and one (21) of the disks comes to rest against the head. Each disk has row of teeth (213 & 223) extending along the edge of the concave side and a bore (211 & 221) through the center. The shaft (112) of the pin fits into the bores. The disks can be mounted on the shaft with the teeth on each one facing the teeth on the other. The second disk can be fastened to the shaft.

11 Claims, 3 Drawing Sheets

DEVICE FOR POSTOPERATIVE FIXATION BACK INTO THE CRANIUM OF A PLUG OF BONE REMOVED THEREFROM DURING A SURGICAL OPERATION

BACKGROUND OF THE INVENTION

The present invention concerns a device for postoperative fixation back into the cranium of a plug of bone removed therefrom during a surgical operation.

It is often necessary during brain surgery to remove a plug of bone from the cranium to provide the surgeon with access to the field of operation. The plug is sawed out and must be replaced in the cranium after the operation and fixed thereto. Such plugs have long been fixed back into the rest of the cranium by suturing with loops of steel wire that extend through both and then twisting together the projecting ends of the emplaced loops. The contact between the plug and the rest of the cranium is relatively unstable, however. The two halves do not fuse together very well. The scalp can also become inflamed. Another drawback to such an approach is that the wire considerably distorts the images obtained in postoperative computerized tomography and accordingly impedes definitive interpretation of the soft structures of the brain. Although using nonresorbable and physiologically compatible thread instead of wire does eliminate the last-mentioned drawback, the fixation of the plug to the rest of the skull is still unstable. The two parts can also be fixed with thin plates of compatible metal, titanium for instance (EP A 0 510 390). Such plates bridge the abutment between the parts and are screwed to both, also closing off bores introduced into the cranium prior to section. This approach, however, is also not very satisfactory. It is both complicated and time-consuming and hence not inexpensive.

SUMMARY OF THE INVENTION

With the aforesaid state of the art as a point of departure, the object of the present invention is a simpler and more rapid device for accurate and permanent postoperative fixation back into the cranium of a plug of bone removed therefrom during a surgical operation.

This object is attained in accordance with the present invention in a device of the aforesaid genus comprising a pin and two concavoconvex disks of a physiologically compatible metal or metal compound. The pin has a flat head at one end and one of the disks comes to rest against the head. Each disk has row of teeth extending along the edge of the concave side and a bore through the center. The shaft of the pin fits into the bore. The disks can be mounted on the shaft with the teeth on each one facing the teeth on the other. The second disk can be fastened to the shaft.

The inner disks in the aforesaid fixation device in accordance with the present invention are secured to the pins in the vicinity of the head. The disks are then inserted through a slightly larger recess in the circumference of the plug, below the parts of the joint, with the shaft of the pin projecting out of the kerf between the plug and the rest of the cranium. The outer disk is then mounted over the section of pin projecting out of the kerf. The two disks are then approached until their teeth bite into the edges of both the plug and of the rest of the cranium. The second disk is then secured to the shaft.

Titanium is particularly appropriate for the physiologically compatible metal. Such titanium alloys as $Ti_6A_6Va$ are also appropriate. A device made of titanium is of advantage because it will not distort postoperative computerized-tomography images. The inner disk can be mounted more stable on the shaft of the pin if the transition between the head of the pin and the shaft is conical and dimensioned to ensure that a disk resting against the head will be forced tight around the shaft. Slits can also extend radially outward from the bore through the first disk to be mounted on the shaft. The center of the disk can be depressed. Areas can be removed from the disks at regular intervals between the bore and the edge to conserve material. The device can be applied to the two halves of bone by a procedure similar in principle to blind riveting. Notches can accordingly be introduced into each shaft to prevent the second disk mounted thereon from sliding away from the head of the pin. If the second disk on the shaft is deformed in a direction opposite that of its concavoconvexity, the deformation alone will secure it to the shaft by compression. The shaft can also be threaded and accommodate a nut. The nut can be tightened against the second disk. The second disk will in every case be displaced until its teeth engage the two halves of the joint, creating the desired fixation of the plug back into the rest of the cranium at the adjacent edges.

The novel device can be easily and rapidly manipulated and accomplishes the desired accurate and permanent postoperative fixation back into the cranium of a plug of bone removed therefrom during a surgical operation.

BRIEF DESCRIPTION OF THE DRAWINGS

The present invention will now be specified with reference to the accompanying drawing wherein.

DESCRIPTION OF THE PREFERRED EMBODIMENTS

Figure 1:
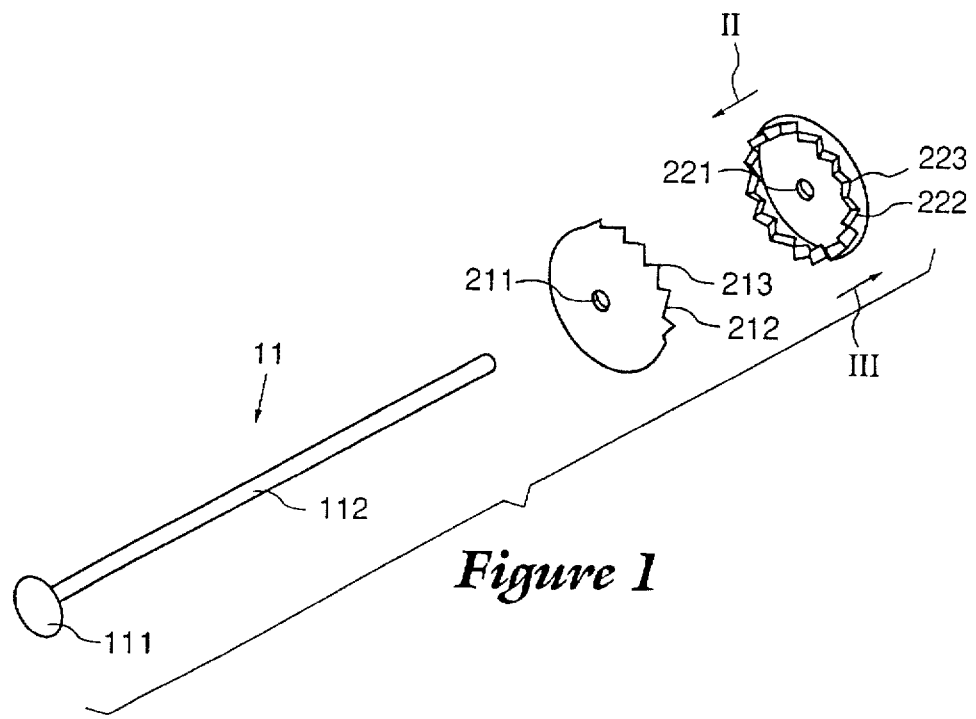
FIG. 1 is an exploded view of the device in accordance with the present invention.
Figure 4:
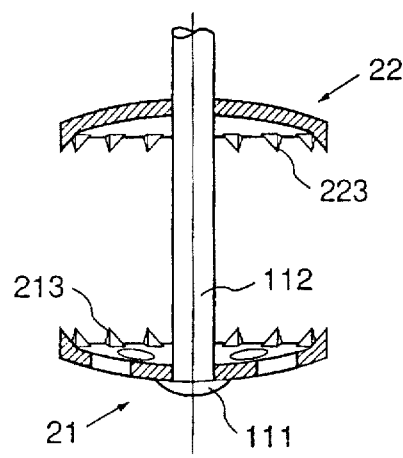
FIG. 4 is a longitudinal section of the components of the device assembled.

A device for postoperatively fixing back into the cranium a plug of bone removed therefrom during a surgical operation comprises a pin 11 and two concavoconvex disks 21 and 22. The pin comprises a shaft 112 and a head 111. Disk 21, the inner disk, is mounted on the shaft first and comes to rest against the inner surface of the plug and of the rest of the cranium that are to be united. Disk 22, the outer disk, is mounted on the shaft next and comes to rest against the outer surface of the plug and the rest of the cranium. There is a hole 211 through the center of each disk 21 and a hole 221 through the center of each disk 22. The shaft 112 of pin 11 extends through the holes 211 and 221 of the disks in the assembled device. A row of teeth 213 extends along the edge 212 of the concave side of disk 21, and a row of teeth 223 extends along the edge 222 of the concave side of disk 22. As will be evident from FIGS. 1 and 4, disks 21 and 22 are mounted on the shaft 112 of pin 11 with their teeth facing each other.

Figure 2:
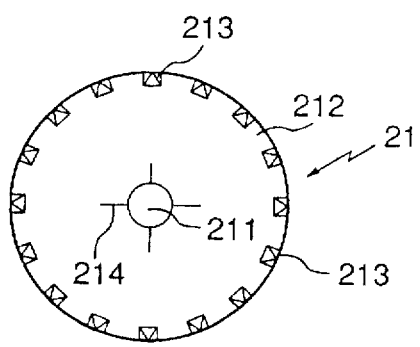
FIG. 2 is a view in the direction indicated by arrow II in FIG. 1 of one embodiment of the first disk mounted over the shaft of the pin.
Figure 3:
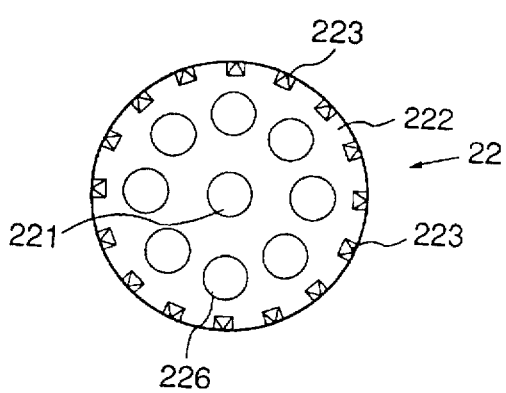
FIG. 3 is a view in the direction indicated by arrow III in FIG. 1 of one embodiment of the second disk mounted over the shaft of the pin.

Shaft 112 fits tightly in the hole 211 through disk 21. Any disk can be provided as illustrated in FIG. 2 with slits 214 extending radially outward from the hole 211 through its center. If the transition between the head 111 and the shaft 112 of pin 11 is conical, slits 214 will as is desirable accurately position the disk in relation to the pin, both of which will accordingly support both the plug and the rest of the cranium once the device has been emplaced. The area between the hole through the center of any disk and its circumference can also be provided as illustrated in FIG. 3 with perforations 226 to conserve material and decrease weight. Each disk can have both slits 214 and perforations 226.

Figure 7:
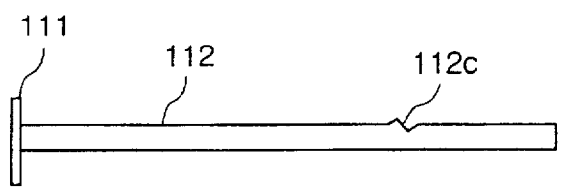
FIG. 7 is a schematic view and shows another embodiment of the present invention.

Thus, in another embodiment of FIG. 7, the shaft 112 of the pin 11 has notches 112c engaging the outer surface of the second disk 22 and force it towards the head 112 of the pin.

Figure 8:
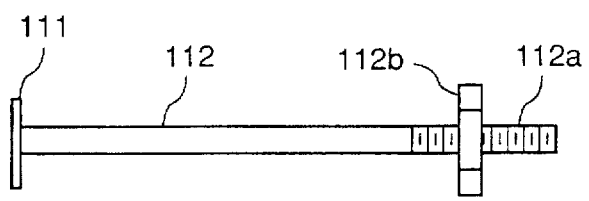
FIG. 8 is a schematic view of a still further embodiment, according to the present invention.

In the embodiment of FIG. 8, the shaft 112 of the pin 11 has a thread 112a and accommodates a nut 112b that can be screwed against the second disk 22.

Figure 5:
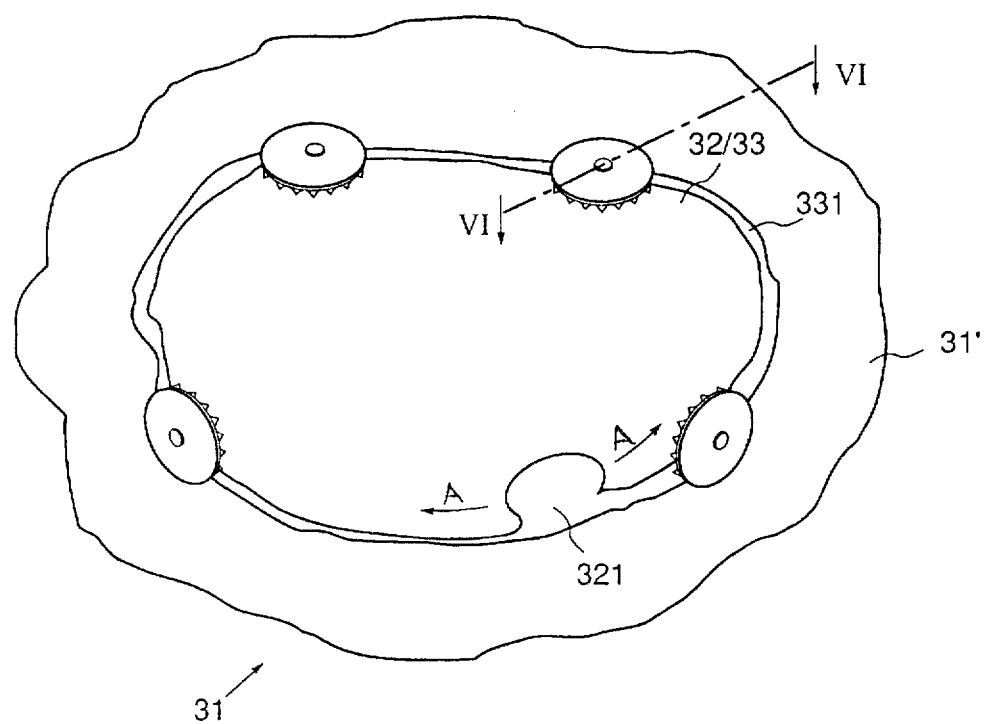
FIG. 5 illustrates how the device in accordance with the present invention can be employed.
Figure 6:
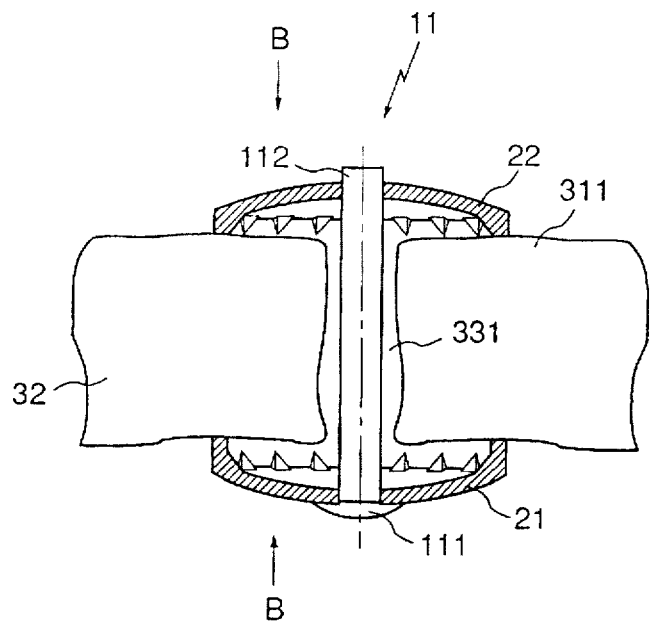
FIG. 6 is a section along the line VI—VI in FIG. 5.

FIGS. 5 and 6 illustrate how the device is employed. FIG. 5 illustrates part of an adult cranium 31 from which a plug 32 of bone has been sawn to provide access to the brain, which is available to the surgeon through aperture 33. A recess 321 slightly larger than the disks has been removed from plug 32 at its circumference. Once the operation is over, the plug is returned to the aperture 33. Inner disks 22 are mounted on the shafts 112 of pins 11. The inner disks are inserted one by one through recess 321 with the shafts projecting out and slid along the inner surface of the plug and residual cranium with the shafts extending out of kerf 331 in the directions indicated by arrows A in FIG. 5 until they arrive at the point where they are to be positioned. Outer disks 22 are now mounted on the shafts of the pins in situ. The outer disks are finally secured to the shafts with a tool of the type employed to fasten blind rivets. The tool forces outer disks 22 and inner disks 21 together in the direction indicated by arrow B in FIG. 6 until the teeth on each disk bite into the tissue of the plug and of the residual cranium, securing the two together. The section of each shaft extending out beyond the outer disk is now trimmed off. The shaft can alternatively be threaded, and the disks forced together over the threads until the teeth bite into the tissue.

I claim:

1. An arrangement for postoperative fixation back into the cranium of a plug of bone removed therefrom during a surgical operation, comprising: a pin and two concavoconvex disks of a physiologically compatible metallic substance; said pin having a flat head at one end, one of said disks resting against said head; each disk having teeth extending along an edge of the concave side and a bore through the center of the disk; said pin having a shaft fitting into said bore; said disks being mounted on said shaft with the teeth of one disk facing the teeth of the other disk, a first one of said disks being mounted adjacent said flat head and the second one of said disks being fastened to said shaft, said plug being fixed back into the cranium without an external device.

2. An arrangement as defined in claim 1, wherein said pin and disks are of titanium.

3. An arrangement as defined in claim 1, wherein said pin and disks are of a physiologically compatible alloy.

4. An arrangement as defined in claim 1, wherein slits extend radially outward from said bore through said first disk.

5. An arrangement as defined in claim 1, wherein said first disk has a center deformed in a direction opposite that of its concavoconvexity.

6. An arrangement as defined in claim 1, including perforations uniformly distributed throughout an area of the disks between said bore through the center of either disk and its circumference.

7. An arrangement as defined in claim 1, wherein said shaft of said pin has notches engaging an outer surface of said second disk and forcing said second disk toward said head of said pin.

8. An arrangement as defined in claim 1, wherein said shaft of said pin is threaded an accommodates-a nut that can be screwed against said second disk.

9. An arrangement as defined in claim 1, wherein slits extend radially outward from said bore through said second disk.

10. An arrangement as defined in claim 1, wherein slits extend radially outward from said bore through said first and second disks.

11. An arrangement for postoperative fixation back into the cranium of a plug of bone removed therefrom during a surgical operation, comprising: a pin and two concavoconvex disks of a physiologically compatible metallic substance; said pin having a flat head at one end, one of said disks resting against said head; each disk having teeth extending along an edge of the concave side and a bore through the center of the disk; said pin having a shaft fitting into said bore; said disks being mounted on said shaft with the teeth of one disk facing the teeth of the other disk, a first one of said disks being mounted adjacent said flat head and the second one of said disks being fastened to said shaft, said plug being fixed back into the cranium without an external device; said pin and disks being of titanium; said first disk having slits extending radially outward from said bore; said first disk being deformed in a direction opposite that of its concavoconvexity; perforations uniformly distributed throughout and area of said disks between said bore through the center of either disk and its circumference; said shaft of said pin having notches engaging an outer surface of said second disk and forcing said second disk toward said head of said pin.

\* \* \* \* \*